US008894798B2

(12) United States Patent
Sakaguchi et al.

(10) Patent No.: US 8,894,798 B2
(45) Date of Patent: Nov. 25, 2014

(54) METHOD AND APPARATUS FOR MANUFACTURING ABSORBENT ARTICLE

(75) Inventors: Satoru Sakaguchi, Kagawa (JP); Yoshikazu Ogasawara, Kagawa (JP); Tomomi Oku, Kagawa (JP); Noriaki Ito, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 639 days.

(21) Appl. No.: 13/141,507

(22) PCT Filed: Dec. 22, 2009

(86) PCT No.: PCT/JP2009/071298
§ 371 (c)(1),
(2), (4) Date: Oct. 4, 2011

(87) PCT Pub. No.: WO2010/074064
PCT Pub. Date: Jul. 1, 2010

(65) Prior Publication Data
US 2012/0024452 A1    Feb. 2, 2012

(30) Foreign Application Priority Data

Dec. 22, 2008 (JP) ................................. 2008-326630

(51) Int. Cl.
*A61F 13/15* (2006.01)
(52) U.S. Cl.
CPC ..... *A61F 13/15804* (2013.01); *A61F 13/15764* (2013.01)
USPC ........................... 156/259; 156/324; 226/109
(58) Field of Classification Search
None
See application file for complete search history.

(56) References Cited

U.S. PATENT DOCUMENTS

| 2004/0108054 A1 | 6/2004 | Otsubo et al. |
| 2004/0182502 A1* | 9/2004 | Wagner et al. ................ 156/204 |

(Continued)

FOREIGN PATENT DOCUMENTS

| EP | 1240881 A2 | 9/2002 |
| EP | 1366734 A1 | 12/2003 |

(Continued)

OTHER PUBLICATIONS

Chinese Office Action as issued on Sep. 5, 2013 in counterpart CN Patent Application No. 200980152139.5.

(Continued)

*Primary Examiner* — Barbara J Musser
(74) *Attorney, Agent, or Firm* — Lowe Hauptman & Ham LLP

(57) ABSTRACT

In a case where components such as side flaps and crotch portions are arranged on multiple webs which are being conveyed while being arranged side by side in the width direction of the webs, articles in various sizes can be handled easily by a web conveying step of conveying a front waistline web 11A and a back waistline web 11B the webs being arranged side by side in a width direction of the webs, a flap attaching step of attaching side flaps 30 onto the web 11 of the front waistline web 11A or the back waistline web, a web gap changing step of changing a gap between the front waistline web 11A and the back waistline web 11B by a web gap changing mechanism 500 and a crotch member attaching step of attaching a crotch member 20 between the front waistline web 11A and the back waistline web 11B, wherein the web gap changing step is performed between the flap attaching step and the crotch member attaching step.

4 Claims, 12 Drawing Sheets

(56) References Cited

U.S. PATENT DOCUMENTS

2006/0030831 A1* 2/2006 Matsuda et al. .............. 604/392
2009/0326503 A1   12/2009 Lakso et al.

FOREIGN PATENT DOCUMENTS

| JP | 4-144558 A | 5/1992 |
| JP | 2001-1029389 A | 2/2001 |
| JP | 2003-102777 A | 4/2003 |
| JP | 2003-339769 A | 12/2003 |
| JP | 2007-030236 A | 2/2007 |
| JP | 2008-508082 T | 3/2008 |
| WO | 0037007 A1 | 6/2000 |
| WO | 2007-133146 A1 | 11/2007 |

OTHER PUBLICATIONS

International Search Report for PCT/JP2009/071298 mailed Apr. 6, 2010.

Extended European Search Report issued Oct. 16, 2013, corresponds to European patent application No. 09834865.9.

* cited by examiner

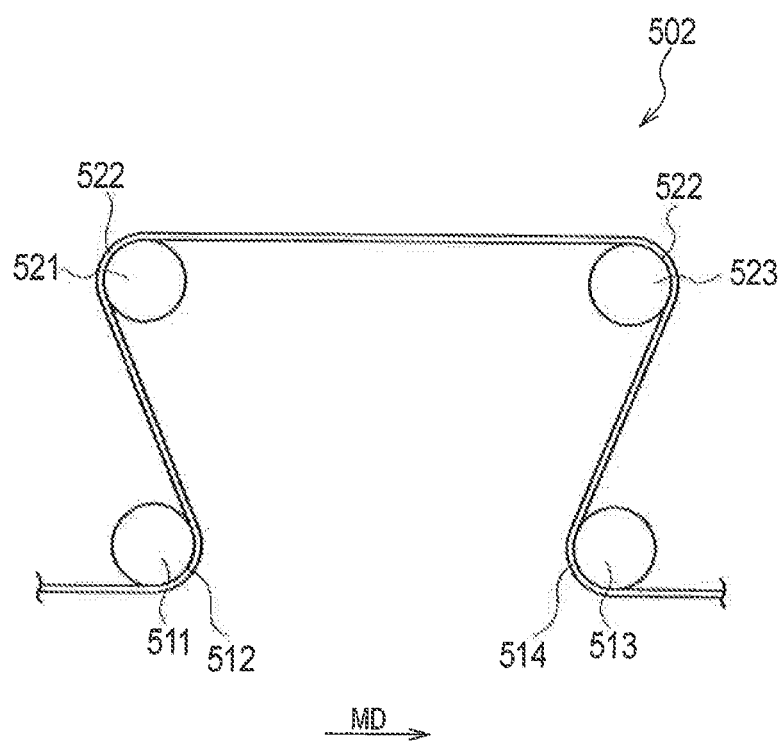

METHOD AND APPARATUS FOR MANUFACTURING ABSORBENT ARTICLE

RELATED APPLICATIONS

The present application is a National Phase of International Application Number PCT/JP2009/071298 and claims priority from, Japanese Application Number 2008-326630, filed Dec. 22, 2008.

TECHNICAL FIELD

The present invention relates to a method and apparatus for manufacturing an absorbent article having a front waistline portion to be fined to the front waistline of a wearer, a back waistline portion to be fitted to the back waistline of the wearer, and a crotch portion to be fitted to the crotch of the wearer, the crotch portion arranged between the front waistline portion and the back waistline portion.

BACKGROUND ART

Conventionally, absorbent articles such as open-type diapers have a vertically long shape extending from the front waistline (ventral portion) to the back waistline (back portion) of a wearer. In general, such absorbent articles include a front waistline portion to be fitted to the front waistline of a wearer, a back waistline portion to be fitted to the back waistline of the wearer, and a crotch portion to be fitted to the crotch of the wearer, the crotch portion arranged between the front waistline portion and the back waistline portion.

The absorbent article also includes side flaps (flap portions) which are used to temporarily attach one of the front waistline portion and the back waistline portion to the other, so that the wearer can easily wear the absorbent article. The side flaps outwardly extend in the width direction of the absorbent article, and is arranged from one of the waistline portions to the other when the wearer wears the absorbent article.

In general, while a strip-shaped front waistline web to be formed into the front waistline portion and a strip-shaped back waistline web to be formed into the back waistline portion are being conveyed in parallel, the side flaps are arranged on one of the front waistline web and the back waistline web alternately at predetermined intervals by a flap transferring mechanism (see, for example, Patent Literature 1).

Moreover, while the front waistline web and the back waistline web are being conveyed in parallel, multiple crotch portion transferring mechanisms arrange the crotch portions at predetermined intervals between the front waistline web and the back waistline web, so that the crotch portions are up side down alternately on the front waistline web and the back waistline web (see, for example, Patent Literature 1).

CITATION LIST

Patent Literature

[Patent Literature 1] Japanese Patent Application Publication 2003-102777 (pp. 2-3, FIG. 4)

SUMMARY OF INVENTION

However, the above-described method for manufacturing an absorbent article includes the following problem. Specifically, when the size of an absorbent article is changed, a gap between a front waistline web and a back waistline web has to be changed.

For this reason, to arrange side flaps and crotch portions on the webs, the positions of the flap transferring mechanisms and the crotch portion transferring mechanism have to be changed. Also, multiple crotch portion transferring mechanisms have to be alternately provided to arrange the crotch portions alternately up side down on the front waistline web and the hack waistline web.

As described above, the changing of the gap between the front waistline web and the back waistline web requires a change in the positions of devices for arranging components forming an absorbent article, such as side flaps and a crotch portion, and the position of a web conveying mechanism including multiple rollers which are each arranged for conveying at least one of the webs. This requires complicated works, and thus the time required for the work becomes long.

In view of the above problems, an object of the present invention is to provide a method and apparatus for manufacturing an absorbent article in which absorbent articles in various sizes can be handled easily in a case where components such as side flaps and crotch portions are arranged on multiple webs which are being conveyed while being arranged side by side in the width direction of the webs.

In order to solve the above problems, the present invention has the following characteristics. A first characteristic of the present invention is a method for manufacturing an absorbent article including a front waistline portion (front waistline portion 10A) to be fitted to a front waistline of a wearer, a back waistline portion (back waistline portion 10B) to be fitted to a back waistline of the wearer, and a crotch portion (crotch portion 20) to be fitted to a crotch of the wearer, the crotch portion arranged between the front waistline portion and the back waistline portion, the method comprising: a web conveying step of conveying a strip-shaped front waistline web (front waistline web 11A) to be formed into the front waistline portion and a strip-shaped back waistline web (back waistline web 11B) to be formed into the back waistline portion by a web conveying mechanism with the webs being arranged side by side in a width direction of the webs (webs 11); a flap attaching step of attaching a flap portion (side flap 30) onto an longitudinal end portion of a waistline portion (waistline portion 10) of one of the front waistline web and the back waistline web, the flap attached to be temporarily attached to the other waistline portion when being worn; a web gap changing step of changing a gap between the front waistline web and the back waistline web by a web gap changing mechanism (web gap changing mechanism 500); a crotch member attaching step of attaching a crotch member to be formed into the crotch portion to a portion between the front waistline web and the hack waistline web. In the method, the web gap changing step is performed between the flap attaching step and the crotch member attaching step.

The characteristics of the present invention can provide a method and apparatus for manufacturing an absorbent article in which absorbent articles in various sizes can be handled easily in a case where components such as side flaps and crotch portions are arranged on multiple webs which are being conveyed while being arranged side by side in the width direction of the webs.

BRIEF DESCRIPTION OF DRAWINGS

FIG. 13 is a side view showing a web gap changing mechanism 502 according to a second modification.

MODES FOR CARRYING OUT THE INVENTION

Figure 1:
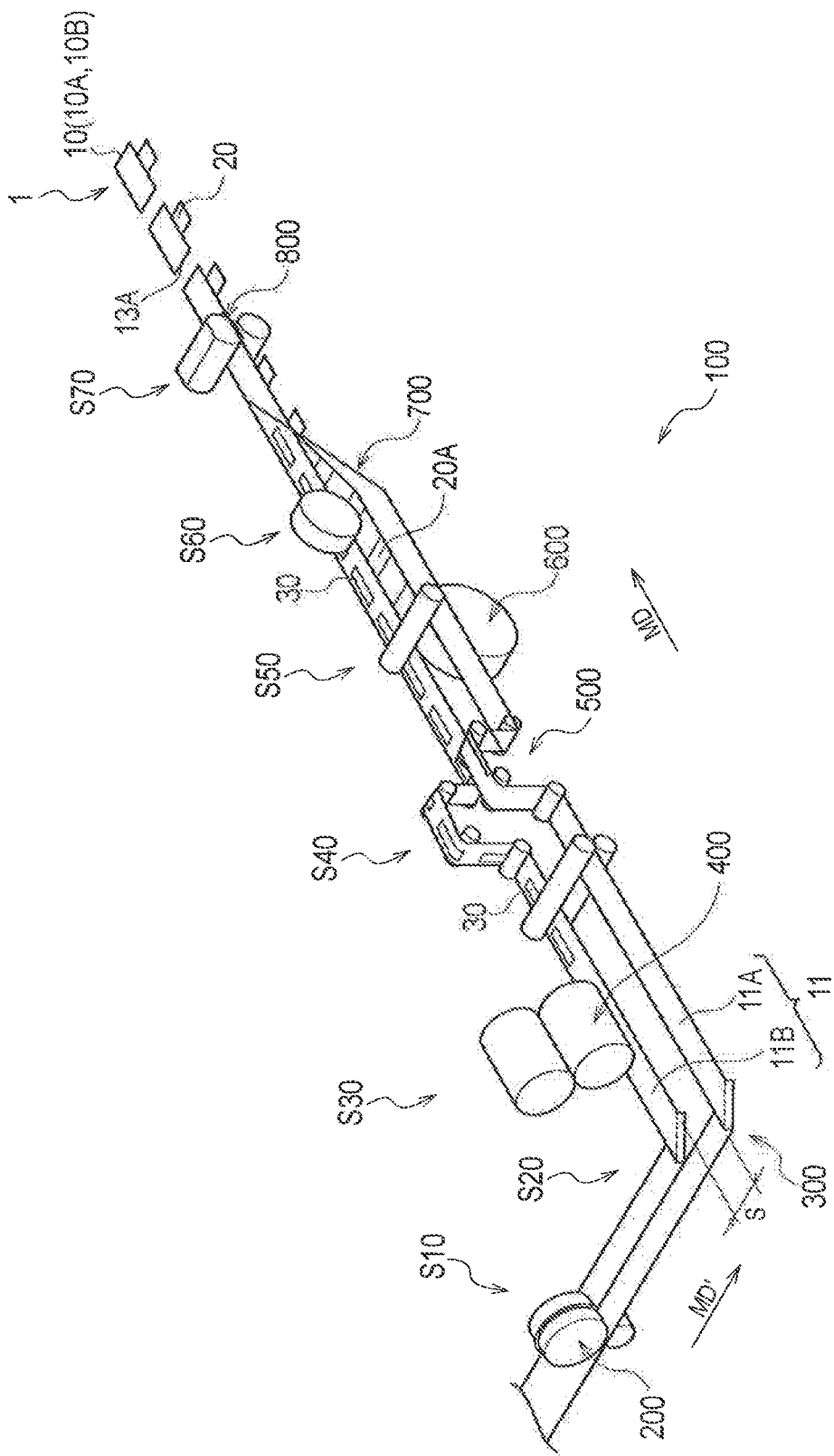
FIG. 1 is a schematic view showing a method for manufacturing an absorbent article according to an embodiment.

An embodiment of the present invention is described by referring to the drawings.

In the following description of the drawings, same or similar reference numerals are given to denote same or similar portions. However, it should be noted that the drawings are merely schematically shown and proportions of dimensions and the like are different from actual ones.

Thus, specific dimensions and the like should be judged by referring to the description below. Additionally, there are of course portions where dimensional relationships and ratios are different from one drawing to another.

A method for manufacturing an absorbent article according to the present embodiment is described by referring to the drawings. FIG. 1 is a schematic view showing a method for manufacturing an absorbent article according to the present embodiment. In the present embodiment, an absorbent article 1 is an open-type diaper.

As shown in FIG. 1, the absorbent article 1 is manufactured by the method for manufacturing an absorbent article. The absorbent article 1 has a front waistline portion 10A, a back waistline portion 10B, and a crotch portion 20 between the front waistline portion 10A and the back waistline portion 10B. The front waistline portion 10A, the back waistline portion 10B, and the crotch portion 20 respectively correspond to the front waistline, back waistline, and crotch of a wearer. In the following description, the front waistline portion 10A and the back waistline portion 10B are simply referred to as a waistline member 10.

The absorbent article 1 further includes side flaps 30 (flap members) which are fixed to the back waistline portion 10B to be temporarily attached (locked or bonded) to the front waistline portion 10A by magic tapes (a registered trademark) or adhesive tapes when being worn. The side flaps 30 do not necessarily need to be arranged in the back waistline portion 10B, and may be arranged in the front waistline portion 10A. In this case, the side flaps 30 are fixed to the front waistline portion 10A and are to be temporarily attached to the back waistline portion 10B when being worn.

The method for manufacturing an absorbent article includes at least a front-and-back waistline division step, a web reversing step, a flap attaching step, a web gap changing step, a crotch member attaching step, a fold-back step, and a waistline side portion cutting step.

At step S10 of the front-and-back waistline division step, a strip-shaped web 11 is divided in the width-direction center portion of the web 11 by a web division mechanism 200 into a strip-shaped front waistline web 11A to be formed into the front waistline portion 10A and a strip-shaped back waistline web 11B to be formed into the back waistline portion 10B. The width-direction center portion of the web 11 indicates a region including the center line of the web 11 in the width direction. The front-and-back waistline division step is performed before a web conveying step.

In the front-and-back waistline division step, the web 11 does not necessarily need to be divided in the width-direction center portion of the web 11, and can be of course divided in any portion as necessary.

At step S20 of the web reversing step, a web reversing mechanism 300 (a turn bar) causes the front waistline web 11A and the back waistline web 11B to be reversed, and sets a gap (S) between the front waistline web 11A and the back waistline web 11B in the width direction of the web 11. This causes the conveyance direction MD of the front waistline web 11A and the back waistline web 11B to be rotated by approximately 90°.

Thereafter, the front waistline web 11A and the back waistline web 11B are conveyed while being arranged side by side in the width direction of the web 11 (the web conveying step). Specifically, the front waistline web 11A and the back waistline web 11B are conveyed while being arranged approximately parallel to each other by a web conveying mechanism (unillustrated) such as a transport roller or a belt conveyor.

At step S30 of the flap attaching step, the side flaps 30 are attached on the back waistline web 11B by a flap transferring mechanism 400. The side flaps 30 do not necessarily need to be attached on the back waistline web 11B, and may be attached on the front waistline web 11A.

In the flap attaching step, even when the size of the absorbent article 1 is changed, the flap transferring mechanism 400 attaches the side flaps 30 to the web 11 without a change of the gap (S) between the front waistline web 11A and the back waistline web 11B, so that the positions of the side flaps 30 are kept constant.

At step S40 of the web gap changing step, a web gap changing mechanism 500 changes the gap (S) between the front waistline web 11A and the back waistline web 11B. The web gap changing step is performed after the front-and-back waistline division step and between the flap attaching step and the crotch member attaching step.

At step S50 of the crotch member attaching step, a crotch portion transferring mechanism 600 attaches a crotch member 20A to be formed into the crotch portion 20 to a portion between the front waistline web 11A and the back waistline web 11B.

Thereafter, an outer sheet may be attached to the front waistline web 11A and the back waistline web 11B to cover the joint portion between the front waistline web 11A and the crotch member 20A and the joint portion between the back waistline web 11B and the crotch member 20A.

At step S60 of the fold-back step, a fold-back mechanism 700 causes the crotch portion 20 to be doubled-over so that the front waistline web 11A and the back waistline web 11B are aligned with each other.

At step S70 of the waistline side portion cutting step, a waistline side portion cutting mechanism 800 cuts out a side portion 13A to be fitted to the waist of a wearer with the front waistline web 11A and the back waistline web 11B being aligned with each other. Consequently, the absorbent article 1 is manufactured.

Figure 2:
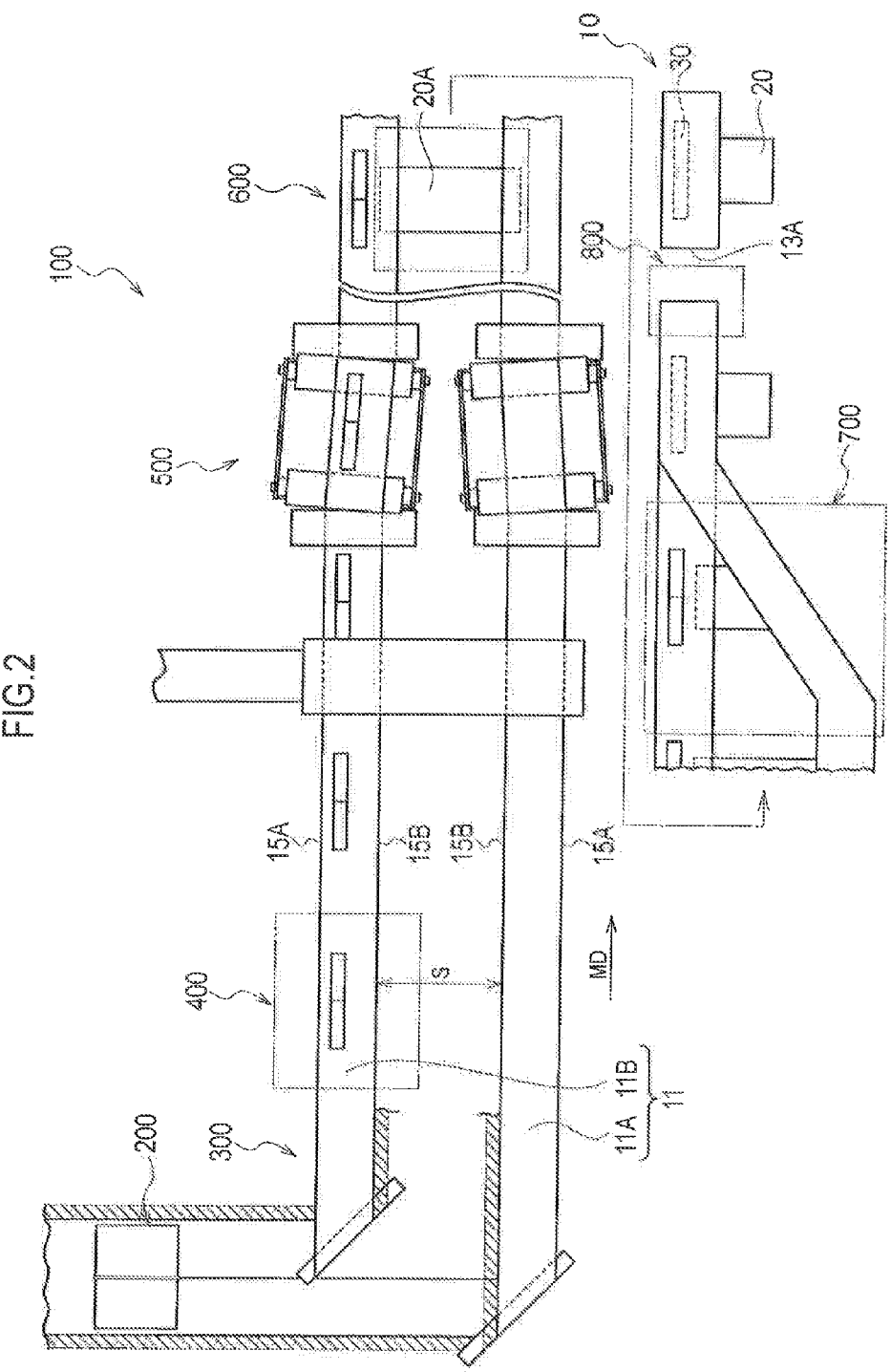
FIG. 2 is a plan view showing an absorbent article manufacturing apparatus 100 according to the embodiment.

The configuration of an absorbent article manufacturing apparatus 100 according to the present embodiment is described by referring to FIGS. 1 and 2. FIG. 2 is a plan view showing the absorbent article manufacturing apparatus 100 according to the present embodiment.

As shown in FIGS. 1 and 2, the absorbent article manufacturing apparatus 100 includes at least the web division mechanism 200, the web reversing mechanism 300, the flap transferring mechanism 400, the web gap changing mechanism 500, the crotch portion transferring mechanism 600, the foldback mechanism 700, and the waistline side portion cutting mechanism 800.

The absorbent article manufacturing apparatus 100 further includes the web conveying mechanism (unillustrated) which conveys the front waistline web 11A and the back waistline web 11B in a state where the webs 11A and 11B are arranged side by side in the width direction of the web 11. The web conveying mechanism is a generally used transport roller, belt conveyor, or the like, and thus the description thereof is omitted.

Figure 3:
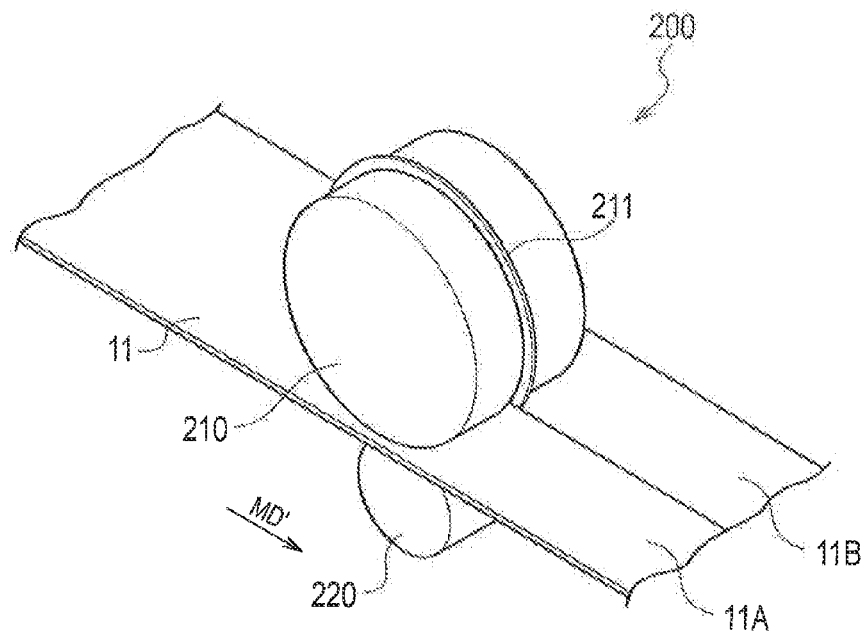
FIG. 3 is a perspective view showing a web division mechanism 200 according to the embodiment.

The above-mentioned web division mechanism 200 is described by referring to the drawings. FIG. 3 is a perspective view showing the web division mechanism 200 according to the present embodiment.

As shown in FIG. 3, in the width-direction center portion of the web 11, the web division mechanism 200 divides the strip-shaped web 11, which is to be divided into the front waistline web 11A and the back waistline web 11B, into the front waistline web 11A and the back waistline web 11B. The strip-shaped web 11 is to be formed into the waist line portion 10.

The web division mechanism 200 includes a main roll 210 which rotates along with the conveyance of the web 11 and an auxiliary roll 220 which is arranged on an opposite side from the main roll 210 across the web 11, and rotates along with the conveyance of the web 11.

The main roll 210 includes a division blade 211 which is arranged on the entire circumference of the main roll 210. Note that the web division mechanism 200 does not necessarily need to include the main roll 210 and the auxiliary roll 220, and only needs to have the configuration with which the web 11 can be divided. For example, the web division mechanism 200 may have the configuration in which only a division blade for dividing the web 11 is arranged in a position corresponding to the center portion of the web 11.

Figure 4:
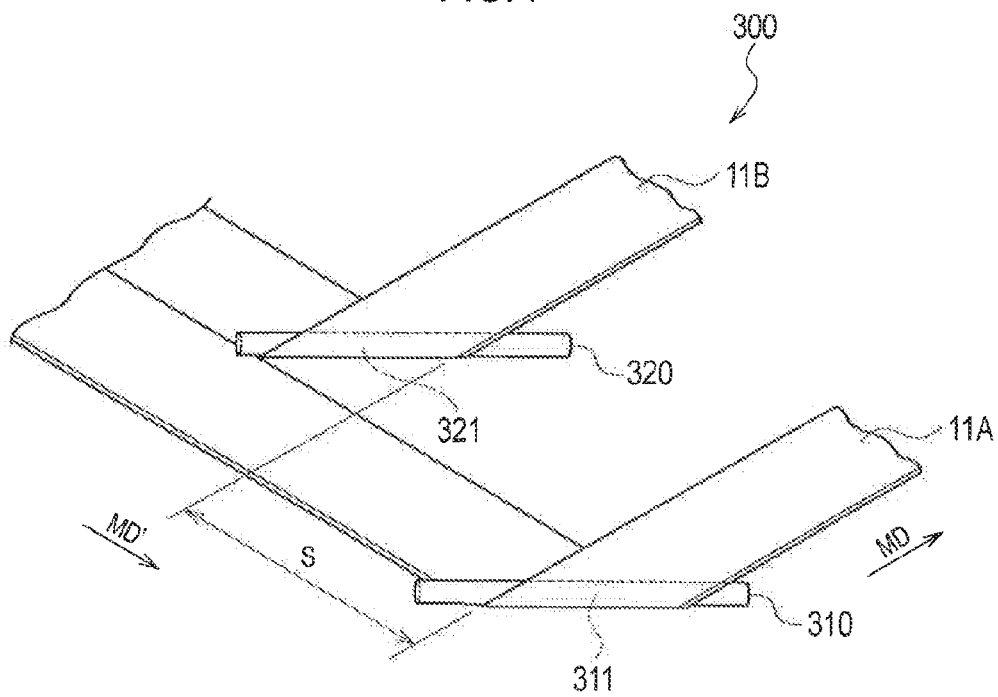
FIG. 4 is a perspective view showing a web reversing mechanism 300 according to the embodiment.

The above-mentioned web reversing mechanism 300 is described by referring to the drawings. FIG. 4 is a perspective view showing the web reversing mechanism 300 according to the present embodiment.

As shown in FIG. 4, the web reversing mechanism 300 causes the front waistline web 11A and the back waistline web 11B to be reversed, and sets a gap (S) between the front waistline web 11A and the back waistline web 11B in the width direction of the web 11. In doing so, the conveyance direction MD of the front waistline web 11A and the back waistline web 11B is rotated by approximately 90°. Accordingly, the front waistline web 11A and the back waistline web 11B are conveyed while being arranged side by side in the width direction of the web 11.

The web reversing mechanism 300 includes a first turn bar 310 (a first bar-shaped portion) having a first contact portion 311 coming in contact with the front waistline web 11A and a second turn bar 320 (a second bar-shaped portion) having a second contact portion 321 coming in contact with the back waistline web 11B.

The first turn bar 310 rotates along with the conveyance of the web 11. The length of the first turn bar 310 is longer than the width of the front waistline web 11A. The first turn bar 310 is arranged forward of the second turn bar 320 in a conveyance direction MD' which is a direction in which the front waistline web 11A is conveyed before the web 11 comes in contact with the first turn bar 310. In the plan view of the web 11 (see FIG. 2), the first turn bar 310 is inclined to the conveyance direction MD' of the web 11 by approximately 45°.

The second turn bar 320 rotates along with the conveyance of the web 11. The length of the second turn bar 320 is longer than the width of the back waistline web 11B. The second turn bar 320 is arranged rearward of the first turn bar 310 in the conveyance direction MD' of the web 11.

In the plan view of the web 11, the second turn bar 320 is inclined to the conveyance direction MD' of the web 11 by the same angle as that of the first turn bar 310 (approximately 45°). In other words, the first turn bar 310 and the second turn bar 320 are inclined to the conveyance direction MD' of the web 11 by angles approximately the same.

The web conveying mechanism (unillustrated) conveys the front waistline web 11A while reversing the front and back surfaces of the front waistline web 11A along the first contact portion 311. In other words, the front waistline web 11A travels on the first contact portion 311 from a lower portion to an upper portion thereof, the first contact portion 311 serving as the outer circumference of the first turn bar 310. As a result, the front waistline web 11A is reversed, and the conveyance direction MD of the front waistline web 11A is rotated by approximately 90°.

Additionally, the web conveying mechanism conveys the back waistline web 11B while reversing the front and back surfaces of the back waistline web 11B along the second contact portion 321. In other words, the back waistline web 11B travels on the second contact portion 321 from a lower portion to an upper portion thereof, the second contact portion 321 serving as the outer circumference of the second turn bar 320. As a result, the back waistline web 11B is revered, and the conveyance direction MD of the back waistline web 11B is rotated by approximately 90°.

Figure 5:
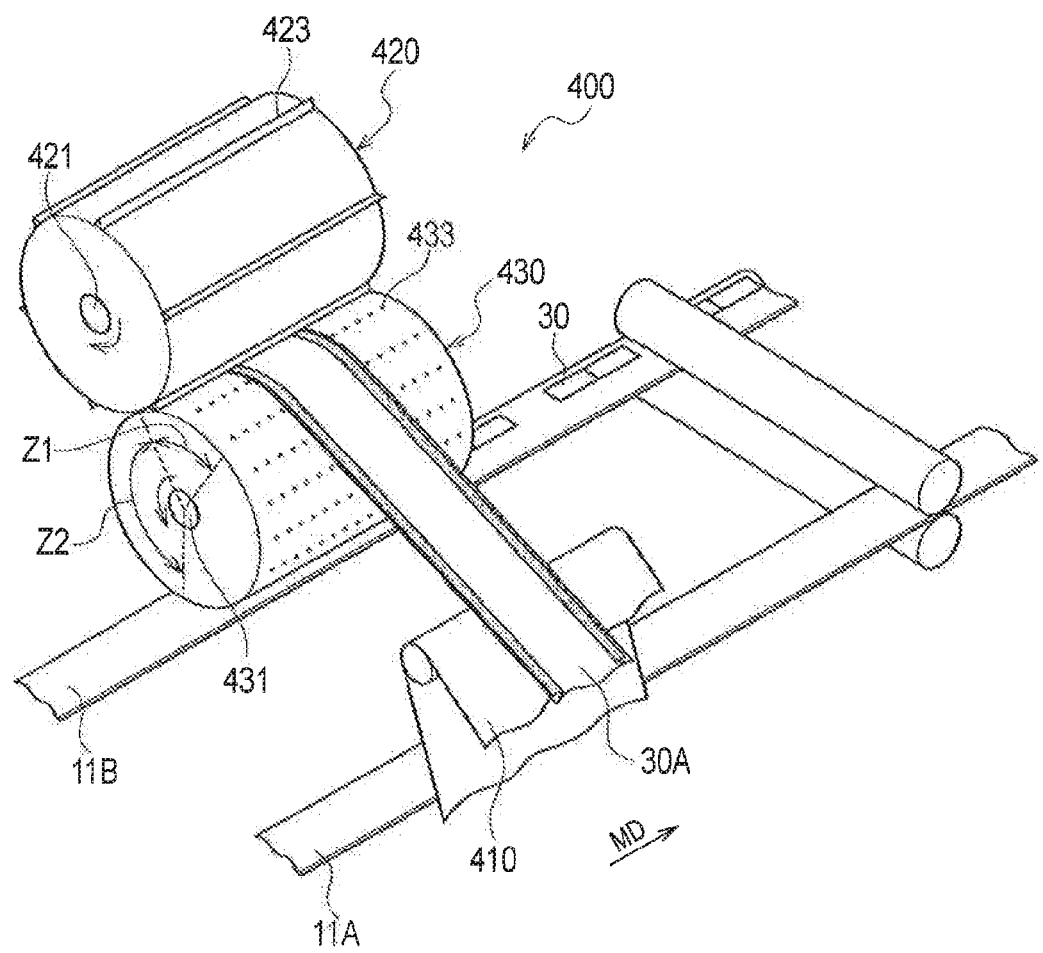
FIG. 5 is a perspective view showing a flap transferring mechanism 400 according to the embodiment.

The above-mentioned flap transferring mechanism 400 is described by referring to the drawings. FIG. 5 is a perspective view showing the flap transferring mechanism 400 according to the present embodiment.

As shown in FIG. 5, the flap transferring mechanism 400 cuts a flap web 30A to be formed into the side flaps 30 at predetermined intervals, the flap web 30A conveyed by an endless belt 410. In addition, the flap transferring mechanism 400 causes the cut flap web 30A to adhere onto the back waistline web 11B by using a thermoplastic resin or the like.

The flap transferring mechanism 400 includes an upper blade roll 420 which rotates around an axial center 421 and a lower blade roll 430 which rotates around an axial center 431.

The upper blade roll 420 has blades 423 which are arranged on the circumference of the upper blade roll 420 at a predetermined interval in a manner approximately parallel to the axial center 421. The lower blade roll 430 has vacuum holes 433 which vacuum the side flaps 30 formed by cutting the flap web 30A and receiving blades (unillustrated) which cut the flap web 30A together with the blades 423.

The circumferential surface of the lower blade roll 430 has a first zone Z1 where the flap web 30A is adhered with a weak adhesion and a second zone Z2 where the side flaps 30 formed by cutting the flap web 30A is adhered with an adhesion stronger than that of the first zone Z1.

When passing through the first zone Z1, the flap web 30A is adsorbed to the circumferential surface of the lower blade roll 430 with the vacuum holes 433 formed in the first zone Z1 while slipping on the circumferential surface of the lower blade roll 430. At this time, the flap web 30A is cut between the blade 423 and the receiving blade, so that the side flaps 30 are formed.

When passing through the second zone Z2, the side flaps 30 are adhered to the circumferential surface of the lower blade roll 430 with the vacuum holes 433 formed in the second zone Z2 without slipping on the circumferential surface of the lower blade roll 430. Thereafter, the side flaps 30 are brought closer to the back waistline web 11B by the lower blade roll 430 and are adhered onto the back waistline web 11B.

Figure 6:
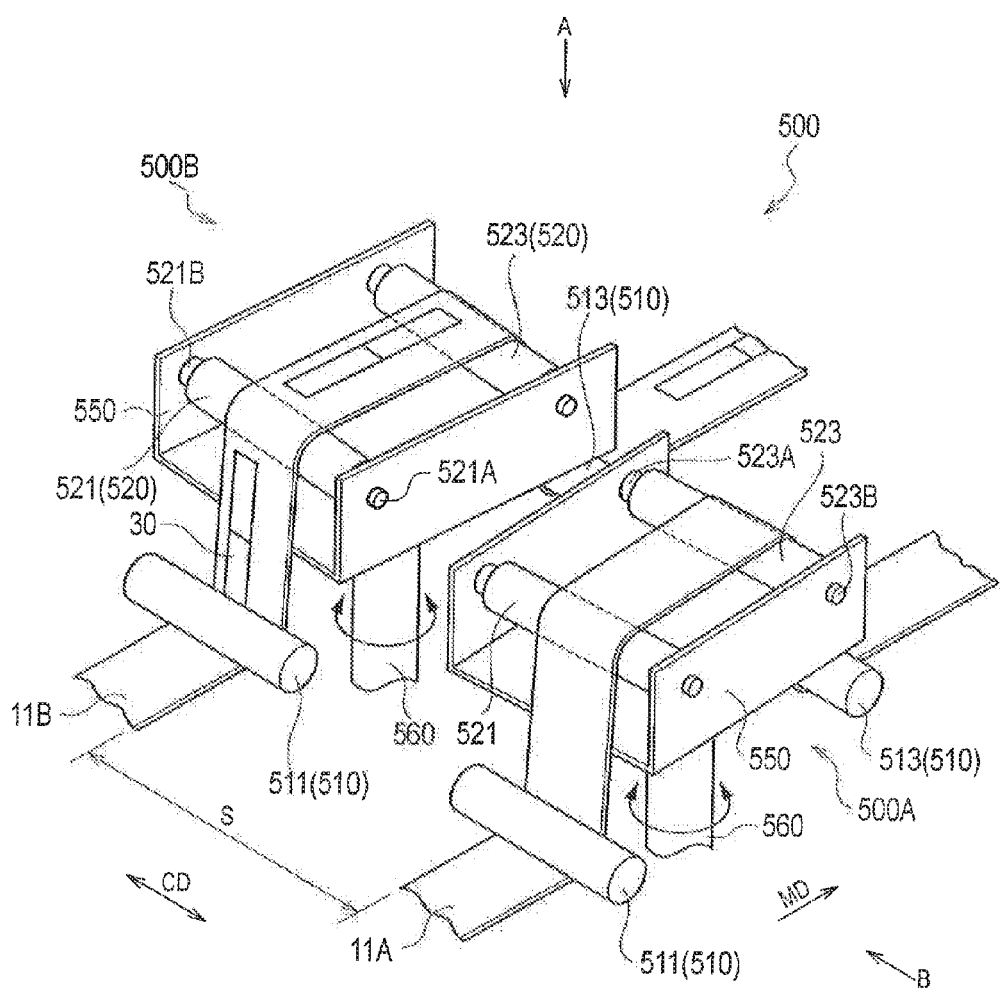
FIG. 6 is a perspective view showing a web gap changing mechanism 500 according to the embodiment.
Figure 7:
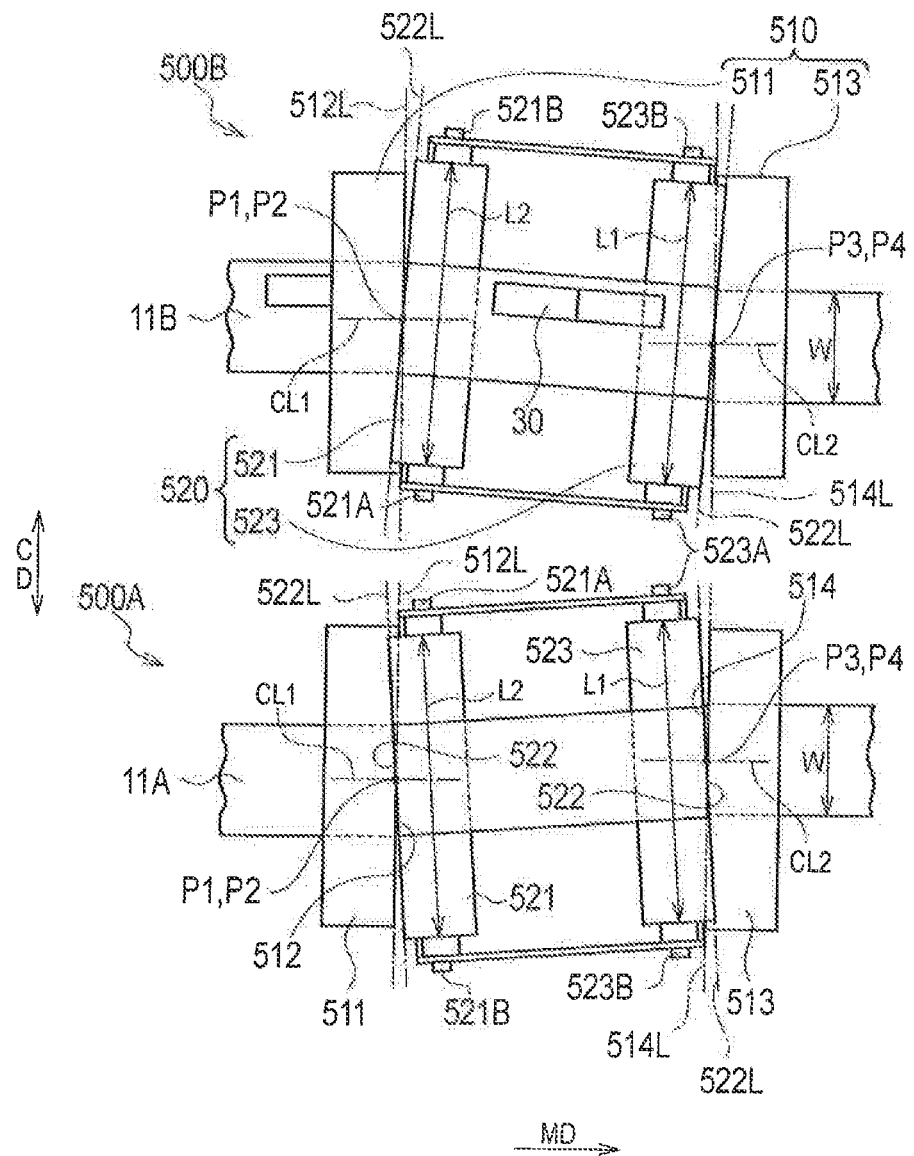
FIG. 7 is a top view (seen from the direction indicated by arrow A in FIG. 6) showing the web gap changing mechanism 500 according to the embodiment.
Figure 8:
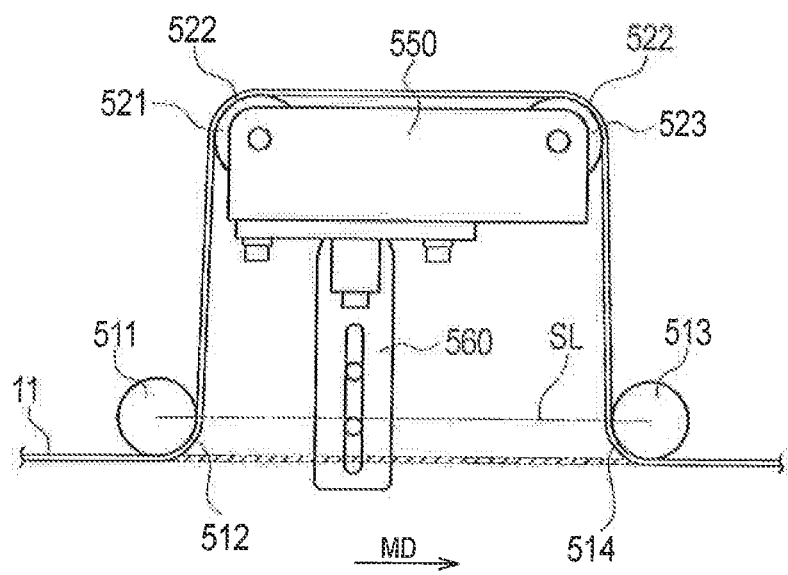
FIG. 8 is a side view (seen from the direction indicated by arrow B in FIG. 6) showing the web gap changing mechanism 500 according to the embodiment.

The above-mentioned web gap changing mechanism 500 is described by referring to the drawings. FIG. 6 is a perspective view showing the web gap changing mechanism 500 according to the present embodiment. FIG. 7 is a top view (seen from the direction indicated by arrow A in FIG. 6) showing the web gap changing mechanism 500 according to the present embodiment. FIG. 8 is a side view (seen from the direction indicated by arrow B in FIG. 6) showing the web gap changing mechanism 500 according to the present embodiment.

As shown in FIGS. 6 to 8, the web gap changing mechanism 500 changes the gap (S) between the front waistline web 11A and the back waistline web 11B which are conveyed by the web conveying mechanism. In the present embodiment, the web gap changing mechanism 500 narrows the gap between the front waistline web 11A and the back waistline web 11B.

The web gap changing mechanism 500 includes a front waist side changing mechanism 500A positioned on the front waistline web 11A side and a back waist side changing mechanism 500A positioned on the back waistline web 11A side, in other words, the web gap changing mechanism 500 is used for both of the front waistline web 11A and the back waistline web 11B.

The web gap changing mechanism 500 (the front waist side changing mechanism 500A and back waist side changing mechanism 500B) includes pairs of web guiding rollers 510 (first web guiding portions) and pairs of web gap changing rollers 520 (second web guiding portions).

The pairs of web guiding rollers 510 are arranged along the conveyance direction MD of the web 11, and rotate along with the conveyance of the web 11. Each of the pairs of web guiding rollers 510 include a front guiding roller 511 which guides the web 11 to the web gap changing rollers 520 and a hack guiding roller 513 which is arranged forward of the front guiding roller 511 in the conveyance direction MD of the web 11 and which guides the web 11 passing through the web gap changing rollers 520 to a crotch portion transferring mechanism 600.

In the plan view of the web 11 (see FIG. 7), each of a first contact line 512L, which extends along a corresponding first contact portion 512 where the web 11 comes in contact with the corresponding front guiding rollers 511 and each of second contact lines 514L which extends along a corresponding second contact portion 514 where the web 11 comes in contact with the corresponding back guiding roller 513 are perpendicular to the conveyance direction MD of the web 11, and extend along the cross direction CD extending along the surface of the web 11.

In other words, in the plan view of the web 11, the axis lines (center lines) of the web guiding rollers 510, i.e. the axis lines of the front guiding roller 511 and the hack guiding roller 513, extends along the cross direction CD.

Each of the pairs of web gap changing rollers 520 is disposed on the conveyance path of the web 11 between the corresponding pair of web guiding rollers 510 (the front guiding roller 511 and back guiding roller 513), and rotates along with the conveyance of the web 11. In the present embodiment, each of the pairs of the web gap changing rollers 520 is disposed between the corresponding pair of web guiding rollers 510 in the plan view of the web 11 (see FIG. 7) and in a view seen from the cross direction CD (see FIG. 8).

Each of the pairs of web gap changing rollers 520 include a front gap changing roller 521 and a back gap changing roller 523 which is arranged forward of the front gap changing roller 521 in the conveyance direction MD of the web 11.

In a view from the cross direction CD, each of the pair of web gap changing rollers 520, i.e. the front gap changing roller 521 and the back gap changing roller 523, is arranged in a portion where a step is to be formed on the web 11 conveyed. Specifically, in the view from the cross direction CD, each pair of web gap changing rollers 520 are arranged at a position off a straight line SE passing through the axial center lines of the corresponding pair of web guiding rollers 510. In the present embodiment, each of the front gap changing rollers 521 and the back gap changing rollers 523 are arranged above the corresponding straight line SL.

In the plan view of the web 11, each of third contact lines 522L which extends along a corresponding third contact surface 522 where the web 11 come into contact with the corresponding web gap changing roller 520 are inclined to the first contact line 512L and the second contact line 514L.

In other words, in the plan view of the web 11, the axis lines (center lines) of the web gap changing rollers 520, i.e. the axis lines of the front gap changing roller 521 and the back gap changing roller 523, are inclined to the axis lines of the front guiding roller 511 and the back guiding roller 513.

In the plan view of the web 11, the axis lines of the front gap changing roller 521 and the back gap changing roller 523 are similarly inclined with respect to the width-direction center portion of the web 11. It is preferable that the inclinations of the axis lines of the front gap changing rollers 521 and the back gap changing rollers 523 be smaller than 45° to the axis lines of the web guiding rollers 510.

In the plan view of the web 11, each of the front gap changing rollers 521 includes a near-end portion 521A which is positioned closer to the side of the other web of the web 11A and 11B arranged side by side in the cross direction CD and a far-end portion 521B which is an end portion on the opposite side from the near-end portion 521A.

In the plan view of the web 11, as shown in FIG. 7, it is preferable that a front changing roller center position P1 which is positioned in the center of each of the front gap changing rollers 521 in the width direction (i.e. the center between the near-end portion 521A and the far-end portion 521B) should overlap a front conveyance roller center position P2 which is positioned in the center of each of the above-described front guiding rollers 511 in the width direction. Note that each of the front change roller center positions P1 is required only to be positioned on a corresponding straight line CL1 which passes through the corresponding front conveyance roller center position P2 and which extends in the conveyance direction MD of the web 11.

In the plan view of the web 11, each of the back gap changing rollers 523 includes a near-end portion 523A which is positioned closer to the side of the other web of the web 11 arranged side by side in the width direction of the web 11 and a far-end portion 523B which is an end portion on the opposite side from the near-end portion 523A. The far-end portion 523B is positioned forward of the near-end portion 523A in the conveyance direction MD of the web 11.

In the plan view of the web 11, it is preferable that a hack changing roller center position P3 which is positioned in the center of each of the back gap changing rollers 523 in the width direction (i.e. the center between the near-end portion 523A and the far-end portion 523B) should overlap a back conveyance roller center position P4 which is positioned in the center of each of the above-described back guiding roller 513 in the width direction. Note that each of the hack changing roller center positions P3 is required only to be positioned on a corresponding straight line CL2 which passes through the corresponding back conveyance roller center position P4 and which extends in the conveyance direction MD of the web 11.

It is preferable that at least the back gap changing roller 523 of each pair of the front gap changing roller 521 and the back gap changing roller 523 have a length (L1) longer than a width (W) of the web 11. In the present embodiment, the length (L1) of each of the back gap changing rollers 523 is approximately the same with the length (L2) of the corresponding front gap changing roller 521.

In addition, each pair of front gap changing roller 521 and the back gap changing roller 523 are rotatably supported by a corresponding frame 550. Each of the frames 550 is coupled to an inclination changing mechanism 560 which is formed of, for example, a rotation motor for changing the inclinations of the axis lines of the corresponding web gap changing rollers 520. In other words, each of the inclination changing mechanism 560 simultaneously changes the axis lines of the corresponding front gap changing roller 521 and back gap changing roller 523 through the corresponding frame 550.

Figure 9:
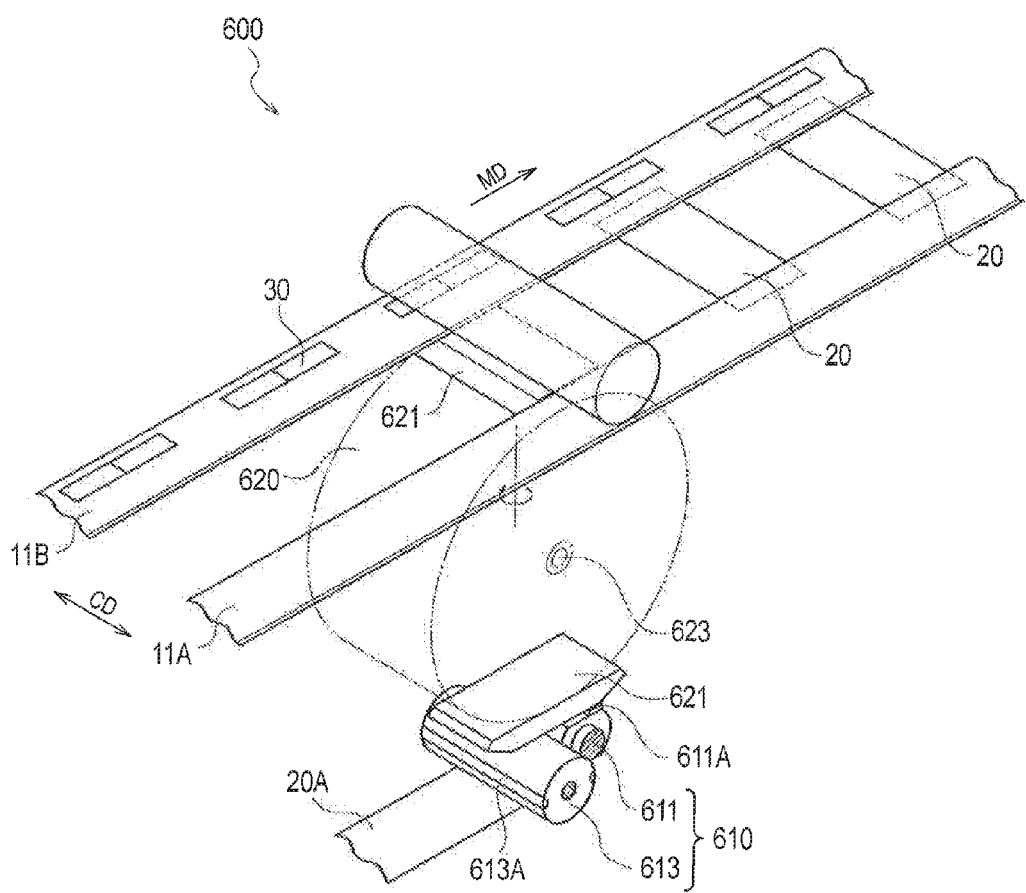
FIG. 9 is a perspective view showing a crotch portion transferring mechanism 600 according to the embodiment.

The above-mentioned crotch portion transferring mechanism 600 is described by referring to the drawings. FIG. 9 is a perspective view showing the crotch portion transferring mechanism 600 according to the present embodiment.

As shown in FIG. 9, the crotch portion transferring mechanism 600 cuts, at a predetermined interval, a crotch member 20A to be formed into the crotch portions 20, the crotch member 20A being formed in advance. The crotch portion transferring mechanism 600 causes the cut crotch portion 20 to be adhered to a portion between the front waistline web 11A and the back waistline web 11B by a thermoplastic resin or the like after rotating the cut crotch portion 20 by 90° and turning it upside down.

The crotch portion transferring mechanism 600 includes a crotch portion cutting roll 610 and a rotation drum 620. The crotch portion cutting roll 610 and the rotation drum 620 rotate around the respective supporting axes (unillustrated).

The crotch portion cutting roll 610 includes a blade roll 611 having a blade 611A and a receiving blade roll 613 having a receiving blade 613A. The blade roll 611 and the receiving blade roll 613 rotate at approximately the same circumferential speed.

The rotation drum 620 has multiple adsorption pads 621 adsorbing the crotch portion 20 cut by the crotch portion cutting roll 610. The rotation of the rotation drum 620 about the supporting shaft 623 causes the crotch portion 20 adsorbed by the adsorption pads 621 to be disposed in a portion between the front waistline web 11A and the back waistline web 11B.

The rotation drum 620 rotates the adsorption pads 621 by 90° by using a rotation mechanism (unillustrated) while the adsorption pads 621 are conveyed upward toward the portion between the front waistline web 11A and the back waistline web 11B. Consequently, the crotch portion transferring mechanism 600 causes the crotch portion 20 to be adhered to the portion between the front waistline web 11A and the back waistline web 11B after rotating the crotch portion 20 by 90° and turning it upside down.

Figure 10:
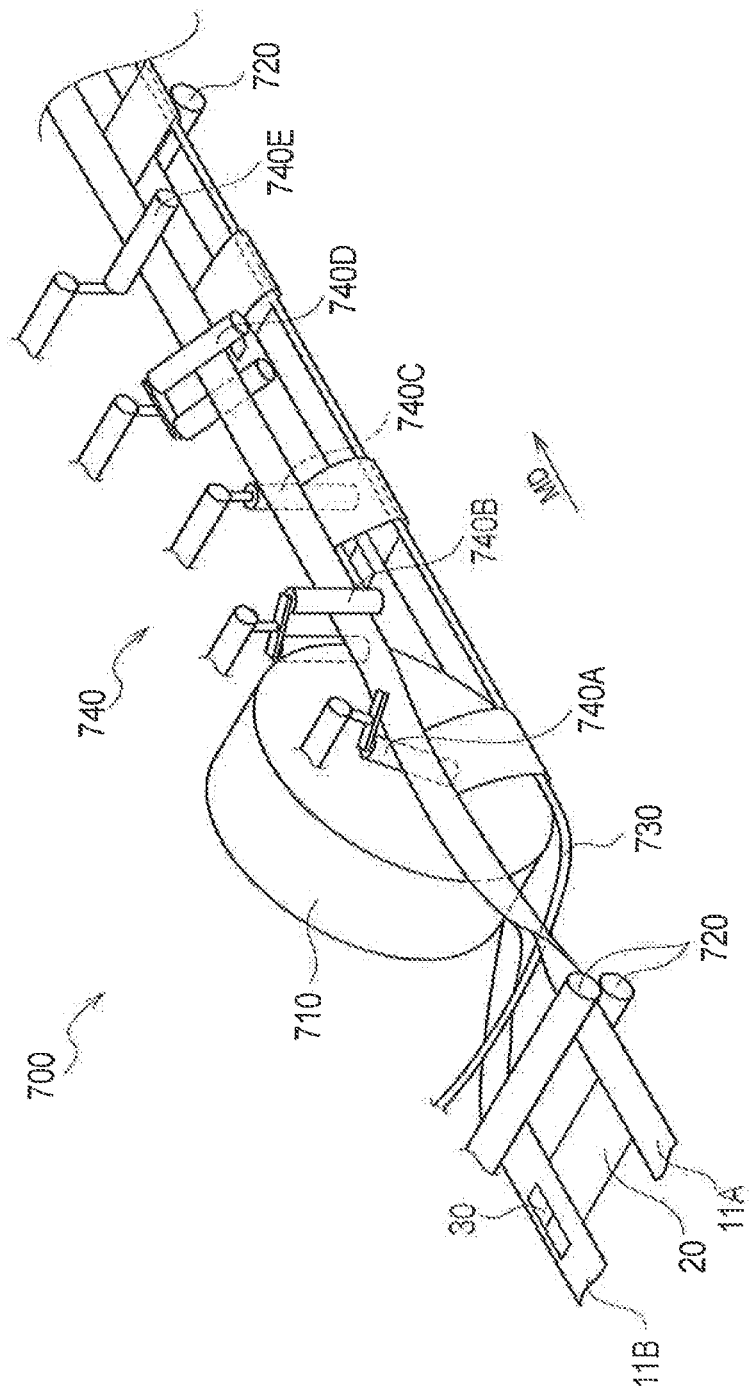
FIG. 10 is a perspective view showing a fold-back mechanism 700 according to the embodiment.

The above-mentioned fold-back mechanism 700 is described by referring to the drawings. FIG. 10 is a perspective view showing the fold-back mechanism 700 according to the present embodiment.

As shown in FIG. 10, the fold-back mechanism 700 causes the crotch portion 20 to be doubled-over so that the front waistline web 11A and the back waistline web 11B are aligned with each other. The fold-back mechanism 700 includes a large-diameter roll 710, conveyance rolls 720, a foldout center bar 730, and guiding rolls 740.

The large-diameter roll 710 maintains the back waistline web 11B and an approximately half of the crotch portion 20 in a horizontal state. The front waistline 11A and the other approximately half of the crotch portion 20 are caused to stand up by a guiding roll 740A to be described later.

The conveyance rolls 720 convey the back waistline web 11B in an approximately horizontal state. In other words, the back waistline web 11B is conveyed in an approximately horizontal state by driving the conveyance rolls 720.

The foldout center bar 730 supports approximately a center of the crotch portion 20 when the crotch portion 20 is folded at an approximately half of the crotch portion 20. The foldout center bar 730 is arranged to be approximately parallel to the back waistline web 11B which is conveyed by the conveyance rolls 720.

The guiding rolls 740 guide the front waistline web 11A so that the front waistline web 11A overlaps the back waistline web 11B. The guiding rolls 740 include, along the conveyance direction, guiding rolls 740A, 740B 740C, 740D, 740D, and 740E.

The guiding roll 740A to 740E are arranged so that the inclined angles of the guiding rolls gradually become smaller as the guiding rolls are disposed more downstream in the conveyance direction MD. Thus, the front waistline web 11A is conveyed while being guided by the guiding roll 740A to 740E, and thereby overlaps the back waistline web 11B through the foldout center bar 730.

Figure 11:
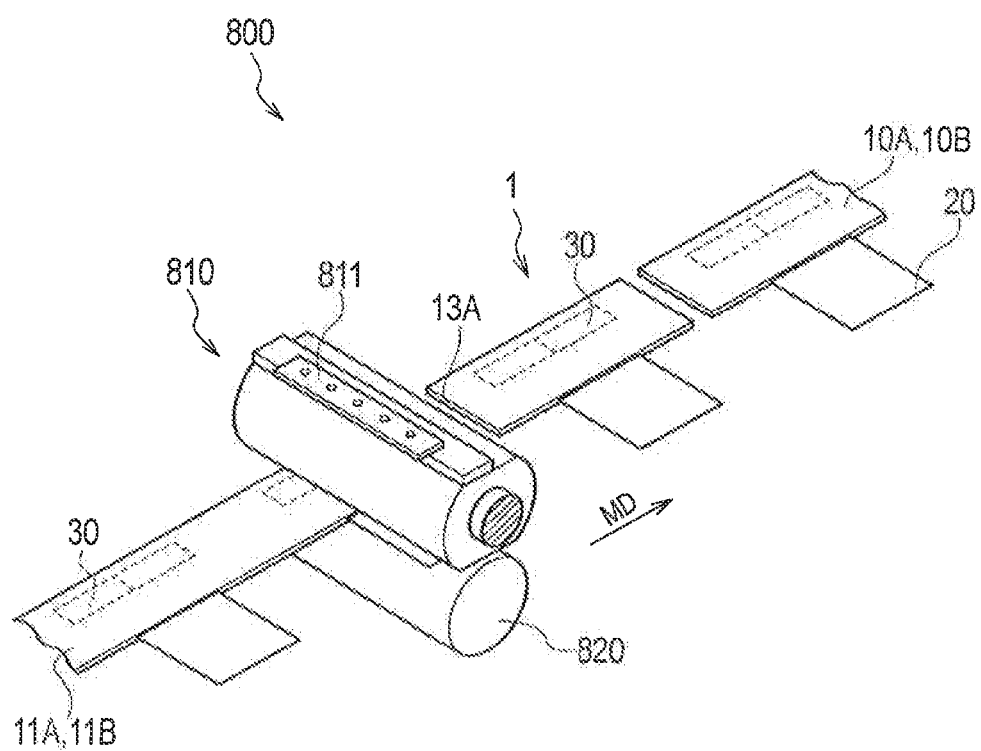
FIG. 11 is a perspective view showing a waistline side portion cutting mechanism 800 according to the embodiment.

The above-mentioned waistline side portion cutting mechanism 800 is described by referring to the drawings. FIG. 11 is a perspective view showing the waistline side portion cutting mechanism 800 according to the present embodiment.

As shown in FIG. 11, the waistline side portion cutting mechanism 800 cuts the web 11 in side portions 13A at predetermined intervals, the side portion 13A to be fitted to the waist of a wearer. Consequently, the absorbent article 1 is manufactured.

The waistline side portion cutting mechanism 800 includes a main roll 810 which rotates along with the conveyance of the web 11 and an auxiliary roll 820 which is arranged on the opposite side from the main roll 810 across the web 11 and rotates along with the conveyance of the web 11.

The main roll 810 has cutting blades 811 disposed at a predetermined interval on the outer circumference of the main roll 810. The auxiliary roll 820 has receiving blades (unillustrated) which are disposed at a predetermined interval on the outer circumference of the auxiliary roll 820. The main roll 810 and the auxiliary roll 820 may be arranged in each of the web pair 11.

The waistline side portion cutting mechanism 800 cuts the web 11 in the side portions 13A to be fitted to the waist of a wearer in a state where the front waistline web 11A and the back waistline web 11B are aligned with each other. Consequently, the absorbent article 1 is manufactured.

In the present embodiment, the web gap changing step is performed between the flap attaching step and the crotch member attaching step. Accordingly, the web gap changing mechanism 500 which is used in the web gap changing step is arranged between the flap transferring mechanism 400 which is used in the flap attaching step and the crotch portion transferring mechanism 600 which is used in the crotch member attaching step. For this reason, even when the gap between the front waistline web 11A and the back waistline web 11B (i.e. the size of the absorbent article 1 is changed) is changed by the web gap changing mechanism 500, the flap transferring mechanism 400 is capable of attaching the side flaps 30 to the web 11 without a change of the gap between the front waistline web 11A and the back waistline web 11B, so that the positions of the side flaps 30 are kept constant. Thus, regardless of the size of the absorbent article 1, there is no need to change the position where the flap transferring mechanism 400 is arranged. Additionally, when the gap between the front waistline web 11A and the back waistline web 11B is changed by the web gap changing mechanism 500, there is no need to change the position where the web conveying mechanism including multiple rollers for conveying at least one of the webs 11A and 11B is arranged or the position where the crotch portion transferring mechanism 600 is arranged.

As described above, the gap between the front waistline web 11A and the back waistline web 11B can be changed without changing the positions of the devices for arranging components forming the absorbent article 1, such as the side flaps 30 and the crotch portion 20, and the position of the web conveying mechanism conveying the web 11. As a result, work required for changing the position of each device is simplified, so that the time required for the work can be prevented from becoming long. Additionally, the absorbent articles 1 in various sizes can be easily handled.

In the present embodiment, the front-and-back waistline division step is performed before the flap attaching step. Accordingly, in a case of changing the width of the waistline portion 10, the width of the front waistline web 11A and the width of the back waistline web 11B can be changed by changing the width of the web 11. Thus, as compared with the case where the front waistline web 11A and the hack waistline web 11B are individually conveyed by different members, space can be saved.

When the width of the waistline portion 10 (the shaded area in FIG. 2) is changed, it is preferable that the web 11 be cut in a state where the width-direction center portion of the web 11 (cutting portion) is secured by the web division mechanism 200. In the web reversing step after the web 11 is cut, the front waistline web 11A and the back waistline web 11B are reversed while the conveyance direction MD of the front waistline web 11A and the back waistline web 11B is changed. Accordingly, one end portion 15A of the web 11 is arranged outside in the width direction of the pair of webs 11 and the other end portion 15B of the web 11 is arranged inside in the width direction of the pair of webs 11, the end portions 15A and 15B formed by cutting the width-direction center portion of the web 11. Thus, in the flap attaching step which is performed after the web reversing step, there is no need to change the position where the flap transferring mechanism 400 is arranged.

In the present embodiment, in the plan view of the web 11, the first turn bar 310 and the second turn bar 320 are inclined by the same angle to the conveyance direction MD' of the web 11. Accordingly, the front and back surfaces of the front waistline web 11A and the back waistline web 11B are reversed, and the conveyance direction MD of the front waistline web 11A and the conveyance direction MD of the back waistline web 11B are changed by the same angle. Thus, the front waistline web 11A and the back waistline web 11B can be securely conveyed in parallel to each other.

In the present embodiment, in the plan view of the web 11, each of the third contact lines 522L are inclined to the corresponding first contact lines 512L and second contact lines 514L. In other words, the axis lines of the web gap changing rollers 520 are inclined to the axis lines of the corresponding web guiding rollers 510. Accordingly, the gap (S) between the front waistline web 11A and the back waistline web 11B can be changed without changing the positions of the devices for arranging components forming the absorbent article 1, such as the side flaps 30 and the crotch portion, and the position of the web conveying mechanism conveying the web 11. As a result, work required for changing the position of each device is simplified, so that the time required for the work can be prevented from becoming long. Additionally, the absorbent articles 1 in various sizes can be easily handled.

In the present embodiment, the web gap changing mechanism 500 is used for both of the front waistline web 11A and the back waistline web 11B. Additionally, in the plan view of the web 11, the axis lines of the front gap changing roller 521 and the back gap changing roller 523 are symmetrically inclined to the width-direction center portion of the web 11. Accordingly, when the gap between the front waistline web 11A and the back waistline web 11B is changed, the conveyance distance of the front waistline web 11A and the conveyance distance of the back waistline web 11B become equal. For example, if the web gap changing mechanism 500 is only arranged for one of the webs 11, the conveyance distances of the one of the webs 11 becomes longer. This causes the one of the webs 11 to be finished more quickly than the other web 11. Thus, when the one of the webs 11 is finished, a new web 11 has to be prepared to replace the web 11 in a state where the other web 11 still remains. This generates wasteful web 11, and thereby the cost is increased by the wasteful web 11. In contrast, as described above, the conveyance distance of the front waistline web 11A and the conveyance distance of the back waistline web 11B are equal, so that no wasteful web 11 is generated and the cost to be increased by the wasteful web 11 can be reduced.

In the present embodiment, the far-end portion 521B in each of the front gap changing roller 521 is positioned downstream of the corresponding near-end portion 521A in the conveyance direction MD of the web 11. In addition, the far-end portion 523B in each of the back gap changing roller 523 is positioned downstream of the corresponding near-end portion 523A in the conveyance direction MD of the web 11. Accordingly, the gap between the front waistline web 11A and the back waistline web 11B can be narrowed.

When the gap between the front waistline web 11A and the back waistline web 11B is not changed, the front waistline web 11A and the back waistline web 11B are directly conveyed from the front guiding rollers 511 to the back guiding rollers 513 (the shaded area in FIG. 8) without passing through the web gap changing rollers 520, respectively. In this case, the web gap changing rollers 520 may be moved to a position under the web guiding rollers 510 (the straight line SL) by the inclination changing mechanisms 560 so that the web 11 may be directly conveyed from the front guiding rollers 511 to the back guiding rollers 513.

In the present embodiment, in the plan view of the web 11, it is preferable that each of the front changing roller center positions P1 may overlap the corresponding front conveyance roller center position P2. In addition, in the plan view of the web 11, it is preferable that each of the back changing roller center position P3 may overlap the corresponding back conveyance roller center position P4. Accordingly, as compared with the case where one center position (P1 or P3) and the other center position (P2 or P4) are not aligned in the width direction of the web 11, the web 11 is prevented from being conveyed in an extended state. Thus, the manufacturing defect of the absorbent article 1 which is caused by conveying the waistline portion 10 in an extended state can be suppressed.

In the present embodiment, it is preferable that the length (L1) of at least the back gap changing roller 523 of each pair of the front gap changing roller 521 and the back gap changing roller 523 be longer than the width (W) of the web 11. Accordingly, even when the axis line of the front gap changing roller 521 or the axis line of the back gap changing roller 523 is greatly inclined from the axis lines of the web guiding rollers 510, the web 11 is securely supported by the web gap changing rollers 520. Thus, the absorbent articles 1 in various sizes, i.e. various gaps between the front waistline web 11A and the back waistline web 11B, can be handled.

In the embodiment, it is preferable that the axis lines of the front gap changing rollers 521 and the axis lines of the back gap changing rollers 523 be each inclined at less than 45° to the corresponding axis lines of the web guiding rollers 510. Note that if the axis lines of the web gap changing rollers 520 are inclined at more than 45° to the axis lines of the web guiding rollers 510, the manufacturing defect of the absorbent article 1 which is caused by conveying the waistline portion 10 in an extended state may not be suppressed.

MODIFICATIONS

The web gap changing mechanism 500 according to the above-described embodiment may be changed as follows. Note that same reference numerals are given to portions same as those of the web gap changing mechanism 500 according to the above-described embodiment, and differences from the above-described embodiment are mainly described.

First Modification

Figure 12:
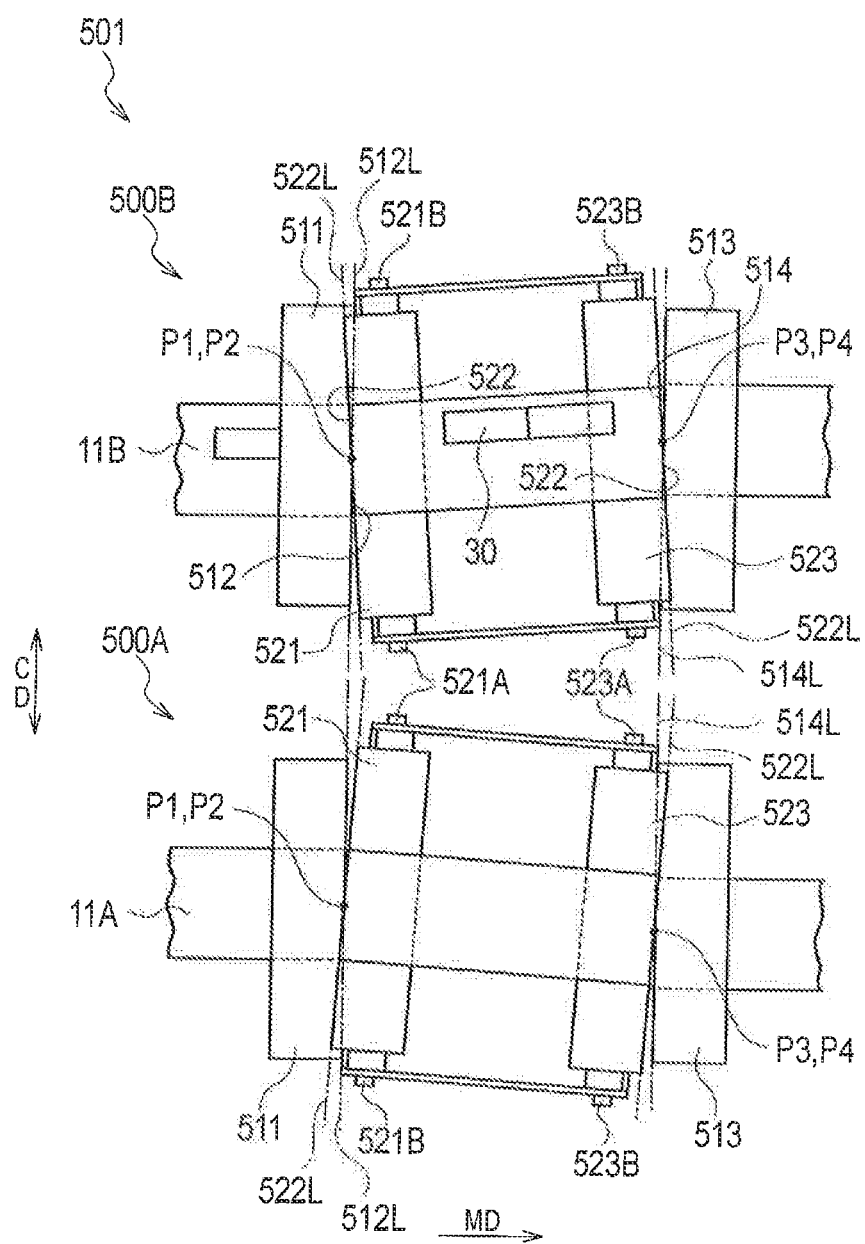
FIG. 12 is a top view showing a web gap changing mechanism 501 according to a first modification.

A web gap changing mechanism 501 according a first modification is described by referring to the drawings. FIG. 12 is a top view showing the web gap changing mechanism 501 according to the first modification.

The web gap changing mechanism 500 according to the above-described embodiment narrows the gap between the front waistline web 11A and the back waistline web 11B. In contrast, the web gap changing mechanism 501 according to the first modification widens the gap between the front waistline web 11A and the back waistline web 11B.

More specifically, as shown in FIG. 12, in each of front gap changing rollers 521 in the web gap changing mechanism 501, a near-end portion 521A is positioned downstream of a far-end portion 521B in the conveyance direction MD of the web 11. Similarly, in each of back gap changing rollers 523 in the web gap changing mechanism 501, a near-end portion 523A is positioned downstream portion of a far-end portion 523B in the conveyance direction MD of the web 11.

Second Modification

A web gap changing mechanism 502 according to a second modification is described by referring to the drawings. FIG. 13 is a side view showing the web gap changing mechanism 502 according to the second modification.

In the web gap changing mechanism 500 according to the above-described embodiment, the each pair of web gap changing rollers 520 is disposed between the corresponding pair of web guiding rollers 510 in the plan view of the web 11 (see FIG. 7). In contrast, in the web gap changing mechanism 502 according to the second modification, web gap changing rollers 520 are not arranged between a pair of web guiding rollers 510.

More specifically, as shown in FIG. 13, in a view from the cross direction CD, a front gap changing roller 521 in the web gap changing mechanism 502 is positioned rearward in the conveyance direction MD of the web 11. Moreover, in a view from the cross direction CD, a back gap changing roller 523 in the web gap changing mechanism 502 is positioned forward in the conveyance direction MD.

Even in this case, the front gap changing roller 521 and the back gap changing roller 523 are arranged between a front guiding roller 511 and a back guiding roller 513 on the conveyance path of the web 11.

Other Embodiments

As described above, the present invention is disclosed by describing the embodiments of the invention. However, it should not be understood that the description and drawings which constitute one part of this disclosure are intended to limit the invention. Various alternative embodiments, examples, and operational techniques are apparent to a person skilled in the art from the disclosure.

For example, the embodiments of the invention may be changed as follows. Specifically, the absorbent article manufacturing method and the absorbent article manufacturing apparatus 100 have been described as the method and apparatus for manufacturing an open-type diaper (an absorbent article 1). However, the invention is not limited to the open-type diaper, and can manufacture absorbent articles other than the open-type diaper, which are required of having various sizes, since a gap between webs 11 to be conveyed in parallel to each other can be changed.

Note that, an order of the method for manufacturing an absorbent article, and the configuration, shape, and arrangement of the apparatus for manufacturing an absorbent article are not particularly limited to those described in the present embodiments, and may be changed as needed depending on a purpose. For example, the absorbent article manufacturing apparatus 100 may further include an outer sheet attaching mechanism.

Additionally, in the above description, the web division mechanism 200 divides the web 11 into the front waistline web 11A and the back waistline web 11B in the width-direction center portion of the web 11. However, the present invention is not limited to this configuration, and the web 11 may be divided into the front waistline web 11A and the back waistline web 11B in a portion other than the width-direction center portion of the web 11.

Moreover, in the above description, the web reversing mechanism 300 includes turn bars (the first and second turn bars 310 and 320) rotating along with the conveyance of the webs 11. However, the present invention is not limited to this configuration, and may have any configuration as long as the conveyance direction MD of the webs 11 is changeable. For example, the turn bars may be a bar-shaped guiding member of cylindrical or prismatic columnar shape.

Furthermore, in the above description, the first turn bar 310 is arranged forward of the second turn bar 320 in the conveyance direction MD' of the web 11. However, the present invention is not limited to this configuration, and the first turn bar 310 only needs to be arranged at a position (for example, rearward of the second turn bar 320 in the conveyance direction MD' of the web 11) different from the position of the second turn bar 320.

Additionally, in the above description, the length of the first turn bar 310 is longer than the width of the front waistline web 11A, and the length of the second turn bar 320 is longer than the width of the back waistline web 11B. However, the present invention is not limited to this configuration, and the lengths of the first turn bar 310 and the second turn bar 320 may be the same or shorter than the width of the respective webs 11.

Moreover, in the above description, the web gap changing mechanism 500 is used for both of the front waistline web 11A and the back waistline web 11B. However, the present invention is not limited to this configuration, and the web gap changing mechanism 500 may be arranged for at least one of the front waistline web 11A and the back waistline web 11B.

Furthermore, in the above description, the web gap changing mechanism 500 includes the pairs of the web gap changing rollers 520 (the front gap changing rollers 521 and the back gap changing rollers 523). However, the present invention is not limited to this configuration, and only at least one roller of each pairs of the web gap changing rollers 520 is needed.

Additionally, in the above description, each of the pairs of web gap changing rollers 520 (the front gap changing roller 521 and the back gap changing roller 523) is arranged above the corresponding pair of web guiding rollers 510, i.e. above the straight line SL. However, the present invention is not limited to this configuration, and each pair of web gap changing rollers 520 may be arranged under the corresponding straight line SL. Note that each pair of web gap changing rollers 520 may be arranged to the left or right of the corresponding straight line. SL when the web gap changing mechanism 500 is arranged in a state of being rotated by approximately 90°.

Moreover, in the above description, the first web guiding portion include the web guiding rollers 510 and the second web guiding portion include the web gap changing rollers 520. However, the present invention is not limited to this configuration, and may have any configuration instead of that using the rollers, as long as the gap between the pair of the webs 11 can be changed. For example, the first and second web guiding portions may each be a bar-shaped guiding member of cylindrical or prismatic columnar shape or multiple members each having cylindrical or prismatic columnar shape which are arranged along the cross direction CD.

As described above, the present invention naturally includes various embodiments which are not described herein. Accordingly, the technical scope of the invention is only defined by the features of the invention according to scope of claims that are adequate from the foregoing description.

Note that, the entirely of Japanese Patent Application 2008-326630 (filed Dec. 22, 2008) is incorporated herein by reference.

INDUSTRIAL APPLICABILITY

The method for manufacturing an absorbent article according to the present invention is effective to be applied in a method for manufacturing absorbent articles such as disposable diapers in various sizes, since a gap between the webs arranged side by side in a direction orthogonal to a conveyance direction can be changed.

The invention claimed is:

1. A method of manufacturing an absorbent article including a front waistline portion to be fitted to a front waistline of a wearer, a back waistline portion to be fitted to a back waistline of the wearer, and a crotch portion to be fitted to a crotch of the wearer, the crotch portion arranged between the front waistline portion and the back waistline portion, the method comprising:
    a front-and-back waistline division step of dividing a strip-shaped web into (i) a front waistline web including the front waistline portion and (ii) a back waistline web including the back waistline portion;
    a web reversing step of reversing the front waistline web and the back waistline web, and concurrently setting a gap between the front waistline web and the back waistline web in a width direction of the front and back waistline webs by a web reversing mechanism;
    a web conveying step of conveying the front waistline web and the back waistline web by a web conveying mechanism, with the front and back waistline webs being arranged side by side in the width direction of the front and back waistline webs;
    a flap attaching step of attaching a flap portion onto one of the front waistline portion of the front waistline web and the back waistline portion of the back waistline web, the flap portion fixed to said one of the front waistline portion and the back waistline portion to be temporarily attached to the other waistline portion when being worn;
    a web gap changing step of changing the gap between the front waistline web and the back waistline web by a web gap changing mechanism; and
    a crotch member attaching step of attaching a crotch member to be formed into the crotch portion to a portion between the front waistline web and the back waistline web,
wherein
    the web gap changing step is performed between the flap attaching step and the crotch member attaching step,
    the front-and-back waistline division step is performed before the web conveying step,
    the web reversing step is performed after the front-and-back waistline division step and before the web conveying step,
    the web reversing mechanism includes:
        a first bar-shaped portion having a first contact portion coming into contact with the front waistline web; and
        a second bar-shaped portion having a second contact portion coming into contact with the back waistline web,
    in a plan view of the front and back waistline webs, positions of the first bar-shaped portion and the second bar-shaped portion are shifted from each other in a web conveyance direction in which the front and back waistline webs are conveyed before coming into contact with the first bar-shaped portion,
    in the plan view of the front and back waistline webs, the first bar-shaped portion and the second bar-shaped portion are inclined with respect to the web conveyance direction by approximately same angles, and
    the web reversing mechanism conveys the front waistline web while reversing front and back surfaces of the front waistline web along the first contact portion, and conveys the back waistline web while reversing front and back surfaces of the back waistline web along the second contact portion.

2. The method for manufacturing an absorbent article according to claim 1, wherein
    the web gap changing mechanism is used for conveying at least one of the front waistline web and the back waistline web, and includes:
        a pair of first web guiding portions arranged in the web conveyance direction; and at least one second web guiding portion arranged between the pair of first web guiding portions on a conveyance path of said at least one of the front and back waistline webs, in a view in the width direction and along a surface of the web, the second web guiding portion is arranged at a position where a step is formed in the conveyance path of the web being conveyed between the pair of first web guiding portions, in the plan view of the web, a first contact line and a second contact line run in the width direction, the first contact line running along a first contact surface on which one of the first web guiding portions and the web come into contact with each other, the second contact line running along a second contact surface on which the other first web guiding portion and the web come into contact with each other, and in the plan view of the web, a third contact line is inclined with respect to the first contact line and the second contact line, the third contact line running along a third contact surface on which the second web guiding portion and the web come into contact with each other.

3. A method of manufacturing an absorbent article including a front waistline portion to be fitted to a waistline of a wearer and a back waistline portion to be fitted to a back waistline of the wearer, the method comprising:

a front-and-back waistline division step of dividing a strip-shaped web into (i) a front waistline web including the front waistline portion and (ii) a back waistline web including the back waistline portion;

a web reversing step of reversing the front waistline web and the back waistline web, and concurrently setting a gap between the front waistline web and the back waistline web in a width direction of the front and back waistline webs by a web reversing mechanism, a web conveying step of conveying the front waistline web and the back waistline web, with the front and back waistline webs being arranged side by side in the width direction of the front and back waistline webs;

a flap attaching step of attaching a flap portion onto one of the front waistline portion of the front waistline web and the back waistline portion of the back waistline web by a flap transferring mechanism, the flap portion fixed to said one of the front waistline portion and the back waistline portion to be temporarily attached to the other waistline portion when being worn; and a web gap changing step of changing the gap between the front waistline web and the back waistline web, wherein the front-and-back waistline division step is performed before the web conveying step, the web reversing step is performed after the front-and-back waistline division step and before the web conveying step, the web reversing mechanism includes:

a first bar-shaped portion having a first contact portion coming into contact with the front waistline web; and a second bar-shaped portion having a second contact portion coming into contact with the back waistline web, in a plan view of the front and back waistline webs, positions of the first bar-shaped portion and the second bar-shaped portion are shifted from each other in a web conveyance direction in which the front and back waistline webs are conveyed before coming into contact with the first bar-shaped portion, in the plan view of the front and back waistline webs, the first bar-shaped portion and the second bar-shaped portion are inclined with respect to the web conveyance direction by approximately same angles, the web reversing mechanism conveys the front waistline web while reversing front and back surfaces of the front waistline web along the first contact portion, and conveys the back waistline web while reversing front and back surfaces of the back waistline web along the second contact portion, the web gap changing step is performed after the flap attaching step, and in the flap attaching step, when the size of the absorbent article is changed, the flap transferring mechanism attaches the flap portion to the one of the front and back waistline webs without a change of the gap between the front waistline web and the back waistline web, so that the position of the flap portion is kept constant.

4. An apparatus for manufacturing an absorbent article including a front waistline portion to be fitted to a front waistline of a wearer, a back waistline portion to be fitted to a back waistline of the wearer, and a crotch portion to be fitted to a crotch of the wearer, the crotch portion arranged between the front waistline portion and the back waistline portion, the apparatus comprising:

a web conveying mechanism configured to convey a strip-shaped front waistline web including the front waistline portion and a strip-shaped back waistline web including the back waistline portion, with the front and back waistline webs being arranged side by side in a width direction of the front and back waistline webs; and a web gap changing mechanism configured to change a gap between the front waistline web and the back waistline web which are being conveyed by the web conveying mechanism, wherein the web gap changing mechanism is configured to convey at least one of the front waistline web and the back waistline web, and includes:

a pair of first web guiding portions arranged in a web conveyance direction; and at least one second web guiding portion arranged between the pair of first web guiding portions on a conveyance path of said at least one of the front and back waistline webs, in a view in the width direction, which is perpendicular to the web conveyance direction, and along the surface of the web, the second web guiding portion is arranged at a position where a step is formed in the conveyance path of the web being conveyed between the pair of first web guiding portions, in the plan view of the web, a first contact line and a second contact line run in the width direction, the first contact line running along a first contact surface on which one of the first web guiding portions and the web come into contact with each other, the second contact line running along a second contact surface on which the other of the first web guiding portions and the web come into contact with each other, and in the plan view of the web, a third contact line is inclined with respect to the first contact line and the second contact line, the third contact line running along a third contact surface on which the second web guiding portion and the web come into contact with each other.

* * * * *